United States Patent
Hassan et al.

(10) Patent No.: US 10,065,210 B2
(45) Date of Patent: Sep. 4, 2018

(54) BREACH OR CONTAMINATION INDICATING ARTICLE, OPTIONALLY WITH PRE-WARNING INDICATOR

(71) Applicant: Ansell Limited, Richmond (AU)

(72) Inventors: Noorman Abu Hassan, Shah Alam (MY); Fazli bin Shani, Puchong (MY); Darryl Nazareth, Flanders, NJ (US)

(73) Assignee: Ansell Limited, Victoria (AU)

( * ) Notice: Subject to any disclaimer, the term of this patent is extended or adjusted under 35 U.S.C. 154(b) by 257 days.

(21) Appl. No.: 14/736,830

(22) Filed: Jun. 11, 2015

(65) Prior Publication Data

US 2015/0362435 A1 Dec. 17, 2015

Related U.S. Application Data

(60) Provisional application No. 62/011,173, filed on Jun. 12, 2014.

(51) Int. Cl.
  *B05D 1/18* (2006.01)
  *G01M 3/12* (2006.01)
  (Continued)

(52) U.S. Cl.
  CPC ............... *B05D 1/18* (2013.01); *G01M 3/12* (2013.01); *A41D 19/0058* (2013.01); *G01N 31/22* (2013.01)

(58) Field of Classification Search
  CPC ....... B05D 1/18; G01M 3/12; A41D 19/0058; G01N 31/22
  See application file for complete search history.

(56) References Cited

U.S. PATENT DOCUMENTS

| | | |
|---|---|---|
| 3,947,571 A | 3/1976 | Murphy et al. |
| 4,093,137 A | 6/1978 | Briar et al. |

(Continued)

FOREIGN PATENT DOCUMENTS

| | | | |
|---|---|---|---|
| EP | 1757931 A1 | 2/2007 | |
| WO | WO-94-02080 A1 | 2/1994 | |
| WO | WO2005033229 A1 * | 4/2005 | ........... C09D 107/02 |

OTHER PUBLICATIONS

Tarcha, "Polymers for controlled drug delivery", CRC Press, pp. 39-67, 1991.

(Continued)

*Primary Examiner* — Lore R Jarrett
(74) *Attorney, Agent, or Firm* — Moser Taboada

(57) ABSTRACT

Provided, among other things, is a breach or contamination indicating elastomeric article for indicating a breach or contamination by a selected chemical or group of chemicals, the article having an exterior and interior and comprising: (1) an interior elastomeric layer selected to resist permeation by the selected chemical(s); and (2) exterior thereto, a contiguous or dis-contiguous first indicating layer comprising a dye or pigment and an opacifying agent, the dye or pigment providing the layer with color, the first indicating layer changing color and/or opacity when contacted with a selected chemical such regions of the article where the layer is so contacted contrast with non-contacted regions. A subsequent, interior layer can provide a safety buffer allowing for removal or disposal prior to any potential for harm. A second, interior indicating layer can be used to make the warning louder when a serious breach is occurring.

18 Claims, 5 Drawing Sheets

(51) Int. Cl.
  *G01N 31/22* (2006.01)
  *A41D 19/00* (2006.01)

(56) References Cited

U.S. PATENT DOCUMENTS

| | | | |
|---|---|---|---|
| 4,356,149 A | 10/1982 | Kitajima et al. | |
| 4,480,000 A * | 10/1984 | Watanabe | A61F 13/51498 |
| | | | 428/76 |
| 4,843,014 A | 6/1989 | Cukier et al. | |
| 5,066,436 A | 11/1991 | Komen et al. | |
| 5,133,087 A | 7/1992 | Machida et al. | |
| 5,224,221 A | 7/1993 | Richardson et al. | |
| 5,254,473 A | 10/1993 | Patel | |
| 5,357,636 A * | 10/1994 | Dresdner, Jr. | A41D 19/0058 |
| | | | 2/161.7 |
| 5,411,034 A | 5/1995 | Beck et al. | |
| 5,459,879 A | 10/1995 | Fuchs | |
| 5,549,924 A | 8/1996 | Shlenker et al. | |
| 5,570,475 A | 11/1996 | Nile et al. | |
| 5,650,329 A | 7/1997 | Warner | |
| 5,679,399 A | 10/1997 | Shlenker et al. | |
| 5,976,881 A | 11/1999 | Klingner | |
| 6,060,152 A | 5/2000 | Murchie | |
| 6,060,986 A | 5/2000 | Lederer | |
| 6,175,962 B1 | 1/2001 | Michelson | |
| 6,358,160 B1 | 3/2002 | Winskowicz | |
| 6,391,409 B1 | 5/2002 | Yeh et al. | |
| 6,582,594 B1 * | 6/2003 | Collins | A61K 36/00 |
| | | | 210/502.1 |
| 6,709,725 B1 | 3/2004 | Lai et al. | |
| 7,037,579 B2 | 5/2006 | Hassan et al. | |
| 7,048,884 B2 | 5/2006 | Woodford et al. | |
| 7,378,043 B2 | 5/2008 | Hassan et al. | |
| 7,585,526 B2 | 9/2009 | Hamann | |
| 7,803,438 B2 | 9/2010 | Flather et al. | |
| 2002/0091347 A1 | 7/2002 | Eakin | |
| 2003/0124354 A1 | 7/2003 | Vistins | |
| 2004/0244682 A1 * | 12/2004 | Boler, Jr. | A47L 13/30 |
| | | | 118/264 |
| 2005/0136236 A1 * | 6/2005 | Hassan | B29C 41/14 |
| | | | 428/297.1 |
| 2006/0026737 A1 | 2/2006 | Chen | |
| 2006/0059603 A1 | 3/2006 | Peng et al. | |
| 2007/0154621 A1 * | 7/2007 | Raad | A01N 25/24 |
| | | | 427/2.1 |
| 2011/0287553 A1 | 11/2011 | Hassan et al. | |
| 2015/0037529 A1 | 2/2015 | Loo et al. | |

OTHER PUBLICATIONS

"Chemical Resistance Guide Permeation & Degradation Data", Ansell, 8 Pages, 2008.
International Search Report, dated Mar. 16, 2012 for PCT Application No. PCT/US2011/048589, 10 Pages.
International Search Report, dated Sep. 10, 2015 for PCT Application No. PCT/AU2015/000346, 15 Pages.

* cited by examiner

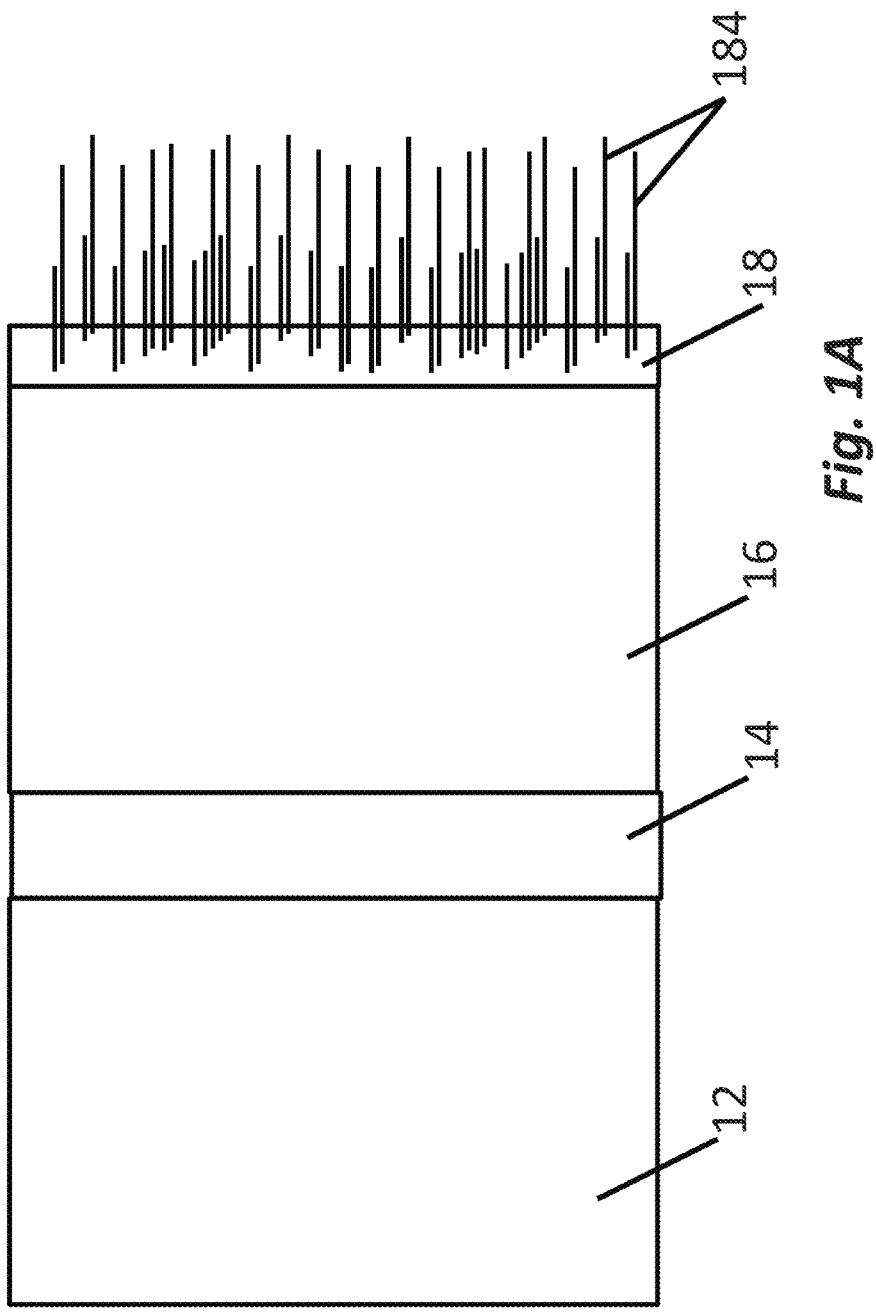

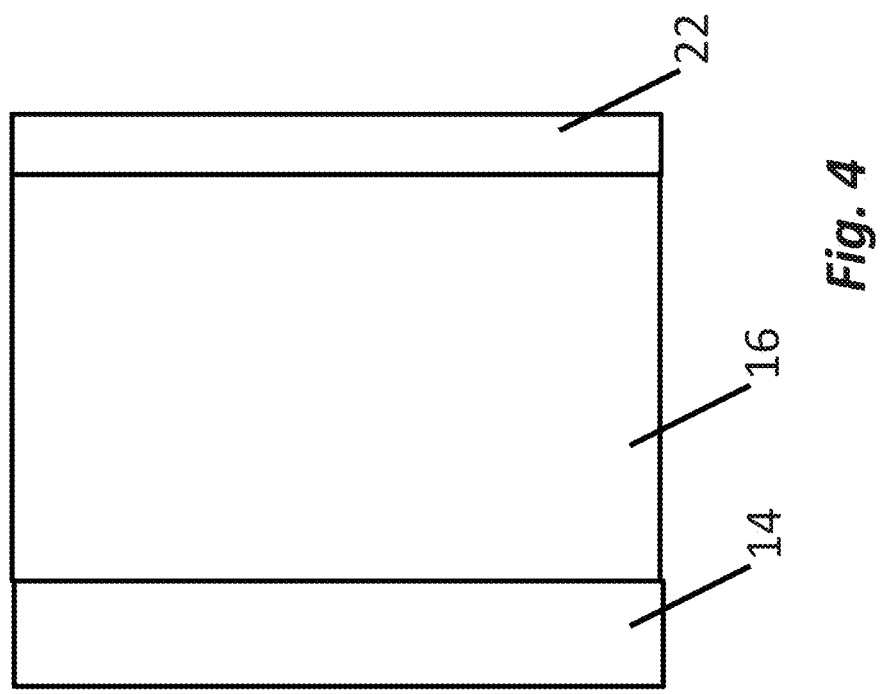

BREACH OR CONTAMINATION INDICATING ARTICLE, OPTIONALLY WITH PRE-WARNING INDICATOR

This application claims the priority of U.S. Ser. No. 62/011,173, filed 12 Jun. 2014, the content of which is incorporated herein in its entirety.

The present application relates generally to protective articles such as gloves, other wearable items and other protective flexible barriers that provide an indication of a chemical and/or mechanical breach of the article's protective surface.

Many workers come into contact with hazardous or pathogenic materials for which protection is desired. For example, industrial workers often come in contact with hazardous chemicals, including organic solvents, acids and bases. Studies indicate that absorption through skin is more dangerous than contact through the lungs. While permeation rates are known for various latex material protective compositions under laboratory testing conditions, a worker may not know when there is a chemical permeation occurring within the protective article during actual use—especially since failure of the protective wear depends on the amount, concentration or type of the contacted chemical and the thickness of the protective product.

It is known in the art that various types of articles can be used to protect individuals from these various hazardous materials. For example, gloves can be provided which protect an individual's hands and/or arms, and condoms can be provided which protect an individual's genitalia and body cavities. Such articles, however, can be compromised due to, for example, chemical permeation, punctures, partial thickness cuts, and the like. Protective articles that provide an indication that an actual breach of this type has occurred will allow the user to remove the article to limit or prevent exposure.

Hassan et al., US Pat. Application 2011/0287553, describes articles with indicator for indicating contamination or breach with microcapsules containing a dye, typically in a hydrophobic material. The microcapsules are believed to give a broad range of sensitivity to contaminating or breaching solvent. Hassan et al., US Pat. Appln. No. 2014/0259332 describes another type of contamination-indicating article. What is needed is a contamination-indicating article that provides two tiers of warning: (a) take caution, and (b) replace immediately. Such an article with a two-tiered warning system has now been found to be available using cost-effective manufacturing methods.

There is a continuing need in the art for improved indicating articles which protect users from hazardous materials.

SUMMARY

Provided for example is a breach or contamination indicating elastomeric article for indicating a breach or contamination by a selected chemical or group of chemicals, the article having an exterior and interior and comprising: (1) an interior elastomeric layer selected to resist permeation by the selected chemical(s); and (2) exterior thereto, a contiguous or dis-contiguous first indicating layer comprising a dye or pigment and an opacifying agent, the dye or pigment providing the layer with color, the first indicating layer changing color and/or opacity when contacted with a selected chemical such regions of the article where the layer is so contacted contrast with non-contacted regions.

Additionally provided, for example, is a method of making an article, such as outlined above, comprising: dipping a former (which may have previously been dipped to form coagulated latex layers) into a polymer dispersion for forming an elastomeric layer, which may be the interior elastomeric layer; and further dipping the former into a polymer dispersion comprising the dye and opacifying agent for forming the first indicating layer.

Further provided, for example, is a breach or contamination indicating elastomeric article for indicating a breach or contamination by a selected chemical or group of chemicals, the article having an exterior and interior and comprising: an elastomeric layer selected to resist permeation by the selected chemical(s); interior thereto, a contiguous or dis-contiguous interior indicating layer, which interior indicating layer comprises particles of a lysochrome dye, the particles selected to become more visually impactful as a selected chemical penetrates to contact lysochrome dye particles; and one or more of: (a) between the elastomeric layer and the interior indicating layer, a wax residue of a wax primer; and (b) wherein the interior indicating layer anchors fibers for an interior liner, the fibers configured to improve comfort for a user and/or moisture dispersion from a user.

Additionally provided, for example, is a method of making an article, such as outlined above, comprising: dipping a former (which may have previously been dipped to form coagulated latex layers) into a polymer dispersion for forming the elastomeric layer; and further dipping the former into a polymer dispersion comprising the lysochrome dye particles, wherein if the interior indicating layer anchors fibers, the fibers are applied as part of a composite dispersion with the lysochrome dye particles.

Further provided, for example, is a method of forming an indicating layer for a breach or contamination indicating elastomeric article comprising: dipping a former (which may have previously been dipped to form coagulated latex layers) into a polymer dispersion for forming the elastomeric layer; further dipping the former into a wax and diluted acid primer; and further dipping the former into a polymer dispersion comprising the lysochrome dye.

DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only illustrative embodiments of this invention and are therefore not to be considered limiting of its scope, for the invention may admit to other equally effective embodiments.

FIG. 1A depicts a cross-section of an article according to the invention;

FIG. 4 shows an embodiment of the article for use in a patch.

Figure 1B:
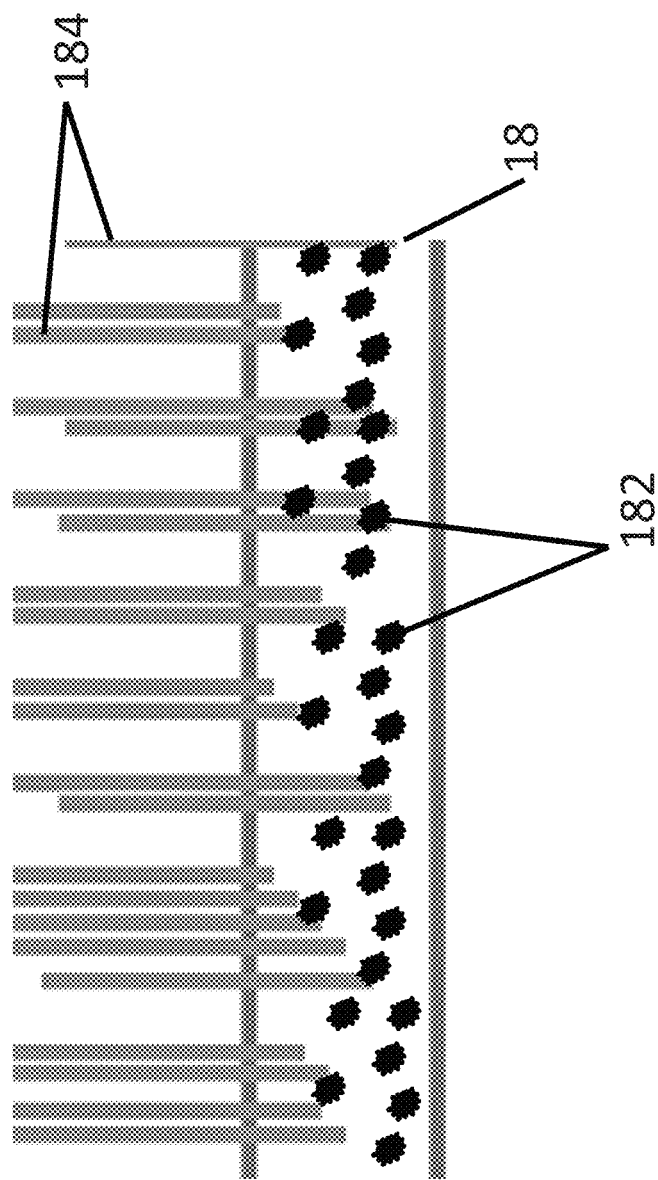
FIG. 1B shows a blow-up of a portion of FIG. 1A.

To facilitate understanding, identical reference numerals have been used, where possible, to designate comparable elements that are common to the figures. The figures are not drawn to scale and may be simplified for clarity. It is contemplated that elements and features of one embodiment may be beneficially incorporated in other embodiments without further recitation.

DETAILED DESCRIPTION

As one of skill in the art will recognize, the point of breach of an industrial glove is generally reached upon solvent exposure near the protective (e.g., outer) layer's permeation breakthrough time, which is generally dependent on the protective layer's thickness and degree of chemical resistance. However, estimations of breakthrough time measured on unflexed gloves may be unreliable because flexing is known to affect breakthrough time. The use of an indicating layer overcomes this problem since a breach of the glove can be immediately detected, whether in the flexed or unflexed state. Real breakthrough may not match the analytical breakthrough time measured for example as per EN 374-3 (European Standards) testing.

In one embodiment article of the invention, as illustrated in FIG. 1A, there is an exterior elastomeric layer 12, a first indicating layer 14, an interior elastomeric layer 16, and an interior indicating layer 18, which can in embodiments bind fibers 184 that line the article. In the first indicating layer 14 are one or more opacifying agents and dye or pigment. The polymeric content of first indicating layer 14 is selected to be swellable when contacted with xylene, butyl acetate, Methyl Isobutyl Ketone (MIBK), acetone and toluene ("test chemicals"). In embodiments, in addition to detecting the test chemicals, the interior indicating layer detects one or more of hexane, cyclohexane, methanol, acetonitrile and acetic acid ("secondary test chemicals"). The dye or pigment is selected to contrast with a dye or pigment found in interior elastomeric layer.

The first indicating layer 14 can, in embodiments, operate in conjunction with the interior elastomeric layer 16. As the first indicating layer 14 swells from contact with a chemical, without being bound by theory it is believed to become more translucent, such that a color provided by a dye or pigment of the interior elastomeric layer 16 makes more of an impression on the user of the article, or a coworker, or a monitoring camera. The interior elastomeric layer 16 can provide a safety buffer, allowing time for removal or disposal of the article.

The interior indicating layer 18 includes particles of a fat-soluble dye (i.e., lysochrome dye) 182. These particles 182 are indicated schematically (and not to scale) in the blow-up of FIG. 1B by dark dots with uneven borders. As solvent reaches the outer layer of the interior indicating layer 18, the exteriorly located particles are believed to swell and become more visible (without being bound by theory). Given the earlier swelling of the first indicating layer, and possibly other solvent effects on the article, the swollen particles are visible to the user of the article, or a coworker, or a monitoring camera.

Figure 2:
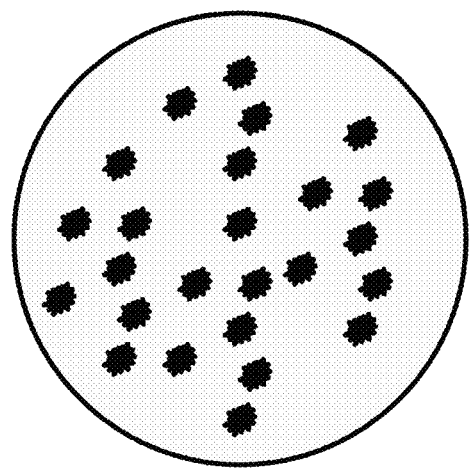
FIG. 2 schematically shows the results of test samples exposed to a time effecting to provide a warning ("yellow"), and to a "red" level indicating immediate article substitution is needed.
Figure 2:
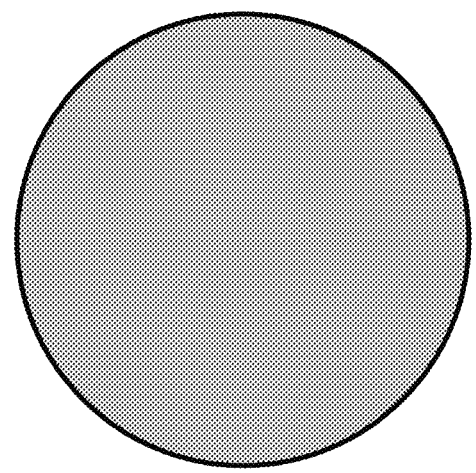
Figure 2:
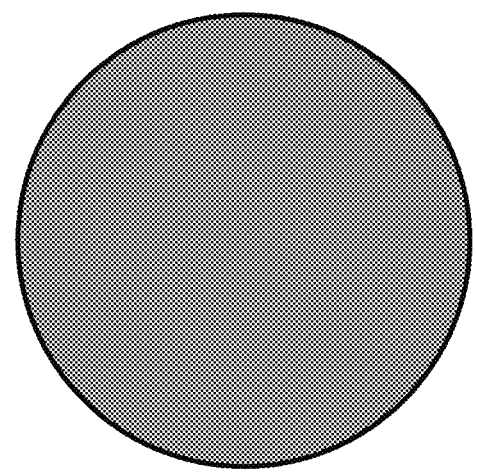
Figure 3:
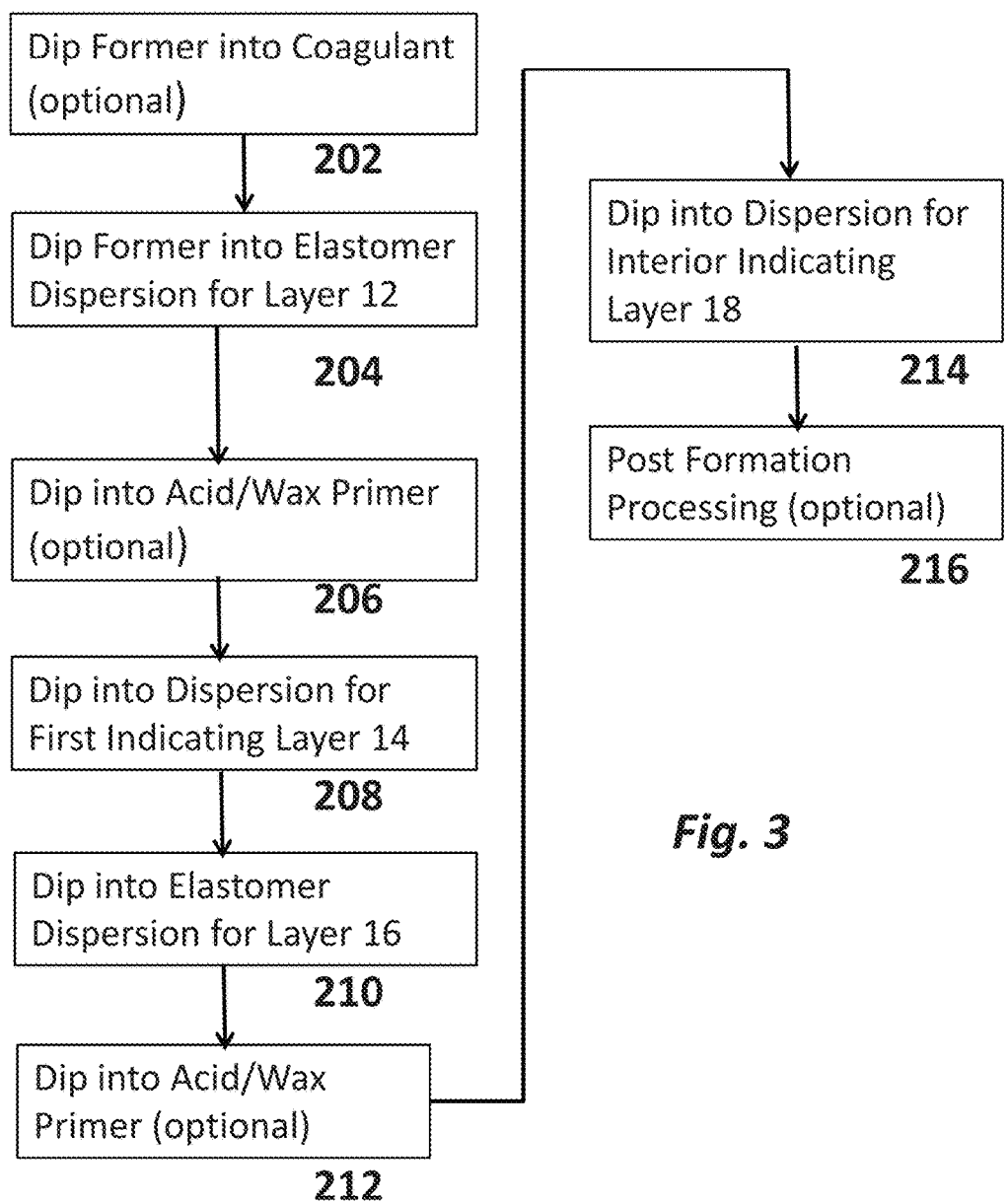
FIG. 3 shows a manufacturing method.

As illustrated in FIG. 2, the first indicating layer 14 provides a change in color tone. In actual use, this change is typically even more apparent because one portion of the article will generally be more affected by solvent than another, so that the change is color tone is noticeable against a background of less or minimal change in color tone. The change in color tone provides a warning to be on alert. In embodiments, the change in tone is to Yellower tones, providing a "yellow" signal. On longer exposure, the particles 182 of the interior indicating layer 18 begin to show, as illustrated. In embodiments, the tone of the article lightens as the particles 182 begin to show.

The exterior elastomeric layer 12 is adapted to be sufficiently translucent that the appearance of color at or about the indicating layer 14, the interior elastomeric layer, and/or the interior indicating layer can be seen from the exterior of the article—such as by the user of the article.

The dye of the particles 182 is selected to be one that as solid particles (e.g., dye precipitate, dye crystals) is sufficiently concentrated so that an amount that is effective in producing color when swollen or solubilized but does not, in the solid form (e.g., dispersed, isolated particles), have a notable color effect when covered by the layers to the exterior—when these are unaffected by solvent.

Those of skill will recognize that additional layers may be present in the embodiment of FIG. 1. For example additional layers may intervene between exterior elastomeric layer 12 and first indicating layer 14, or between indicating layer 14 and interior elastomeric layer 16, or between the interior elastomeric layer 16 and the interior indicating layer 18, so long as such layers do not interfere with the color functions described above. Similarly, there may be additional interior or exterior layers. As noted elsewhere, exterior layer 12 can be very thin (e.g., splash indicating article), or provide more substantial protection from the solvent(s).

A dye that is sufficiently hydrophobic to remain concentrated (and thus not substantially colored) in the indicating layer during aqueous latex dip processing to form the interior elastomeric layer is nonetheless sensitive to a broad range of potential infiltrating solvents. Accordingly, the dye has limited solubility in water.

With Solvex 37-165 nitrile gloves from Ansell (Iselin, N.J.), the permeation rating for several solvents is:

TABLE

| | Polarity Index | Permeation Rating | Dielectric Constant (20° C.) |
| --- | --- | --- | --- |
| Hexane | 0.1 | E | 1.89 |
| Cyclohexane | 0.2 | G-E | 2.023 |
| Xylene | 2.5 | E | 2.27 (para-xylene) |
| Ethyl Ether | 2.8 | E | 4.335 |
| Butyl Acetate | 4.0 | F | |
| Methyl Isobutyl Ketone (MIBK) | 4.2 | P | |
| Methanol | 5.1 | E | 32.63 (25°) |
| Acetonitrile | 5.8 | F | 37.5 |
| Acetic Acid | 6.2 | G | 6.15 |
| Water | 10.2 | E | 78.54 |

(0 = Highly Non-Polar)
(10 = Highly Non-Polar)

In the above, the polarity index is a proprietary, but well recognized in the chemical arts, rating system that provides a relative measure of the degree of interaction of the solvent with various polar test solutes. The permeation rating standard, measured by ASTM Method F739 is:

TABLE

E—excellent protection; permeation rate of <0.9 ug/cm^2/min
VG—very good; permeation rate of <9 ug/cm^2/min
G—good protection; permeation rate of <90 ug/cm^2/min
F—fair protection; permeation rate of <900 ug/cm^2/min
P—poor protection; permeation rate of <9000 ug/cm^2/min
NR—not recommended; permeation rate of >9000 ug/cm^2/min The exterior elastomeric layer is typically formed of a polymer that is resistant to the solvents with which the article is expected to be used. In embodiments, the elastomeric layers (12, 16) are formed of natural rubber (NR), polychloroprene (CR), acrylonitrile butadiene copolymer (NBR) (such as carboxylated acrylonitrile butadiene copolymer), polyisoprene (PI), polyurethane (PU), styrene-butadiene, butyl rubber (copolymer of isobutylene with isoprene, or polymer of isobutylene), or combinations thereof. In embodiments, the elastomeric layers (12, 16) are formed of CR, NBR or combinations thereof. In embodiments, the NBR has a high acrylonitrile content (38% to 42% wt.). In embodiments, the NBR is carboxylated.

Appropriate lysochrome dyes, such as Solvent Red 26 (atomic formula C25H22N4O; scientific name 1-[[2,5-dimethyl-4-[(2-methylphenyl)azo]-phenyl]azo]-2-naphthol; C.I. 26120; AKA Oil Red EGN) or Solvent Red 24, while expected to dissolve and give color well in hexane, have been found to provide indicator with all of the above solvents except water. Thus, it can be expected that a dye providing indicator across all of the representative solvents shall indicate against most solvents with a polarity index of about 0.1 (or less) to about 6.2 (or more), such as in a range from 0.05 to 8. For a dye effective with the representative solvents, it is further expected that for solvents that are not Brønsted-Lowry acids or bases, a dielectric constant (20-25° C.) of about 1.8 to about 45 should provide that the indicator dye is effective. For a dye effective with the representative solvents, it is further expected that for solvents that are Brønsted-Lowry acids or bases, a dielectric constant (20-25° C.) of 1.8 to 12.5 should provide that the indicator dye is effective.

Testing for the above sensitivity to the solvents can be conducted with a material according to FIG. 1 (with or without fibers). An area of the exterior layer can then be contacted with challenge solvent for a period of time sufficient to exceed the time needed for a significant breakthrough with the given solvent. Separable two-part chambers with glass viewing windows, such as used in measuring liquid or vapor breakthrough times can be used.

The invention has been so tested utilizing a NBR (high acrylonitrile) exterior elastomeric layer of about 7 mil, a first indicating layer of about 1-2 mil formed with aliphatic polyurethane and thermoplastic acrylic, an interior elastomeric layer of NBR (high acrylonitrile) of about thickness 7 mil, and an interior indicating layer of about 3 mil, which interior indicating layer adheres a flock liner. Warning (yellow) and danger (red) indicators were seen at:

TABLE

Sample Tests

| Solvent | Warning Time (min) | Danger Time (min) |
|---|---|---|
| Xylene | 15 | 25 |
| Butyl Acetate | 15 | 23 |
| MIBK | 5 | 17 |
| Acetone | 3 | 7 |
| Toluene | 5 | 8 |
| Butyl Alcohol | 240 | 480 |

An alternative measure of dye suitability is provided by consideration of the octanol-water LogD at pH 5.5, and the molar extinction coefficient. For Solvent Red 26, $LogD_{5.5}$ is 7.16, and the extinction coefficient in chloroform is ≥26,000 $M^{-1}\ cm^{-1}$ at a visible wavelength ($\lambda_{max}$ 521 nm). (As reported at sigmaaldrich.com for its Oil Red EGN product.) Solvent Red 26 has the following structure:

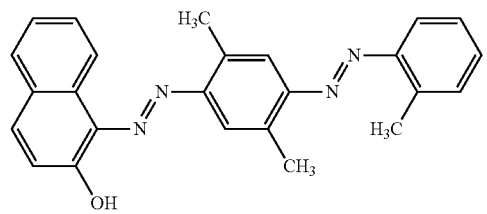 [SMILES: Cc1ccccc1/N=N/c1cc(C)c(/N=N/c2c(O)ccc3ccccc23)cc1C]

It is expected that a Log D (pH 5.5) of about 4 to about 10 can provide a wide range of solvent sensitivities. It is expected that an extinction coefficient in chloroform of greater than about 10,000 $M^{-1}\ cm^{-1}$ can provide a useful color response against an appropriate background.

The lysochrome dye can be incorporated in the elastomeric article in an anionic colloidal environment, since it is believed that an excess of non-ionic or cationic additives in interior indicating layer 18 can promote a tendency for the dye to prematurely swell and migrate during the manufacturing processing of the article.

Solvent Red 24, 1-(2-methyl-4-(2-methylphenyldiazenyl) phenyl) azonapthalen-2-ol, differs by a methyl group:

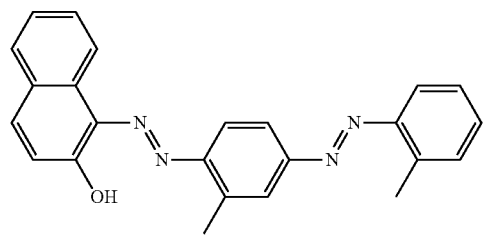 [SMILES: Cc1ccccc1/N=N/c1ccc(/N=N/c2c(O)ccc3ccccc23)c(C)c1]

Dye particles or organic pigments found in the first indicating layer are uniformly wetted such as with anionic surfactants and dispersed, so as to provide a uniform color.

Dye particles in the interior indicating layer 18 can be, on average, about 0.5 to about 4 micron, or about 0.5 to about 2 micron in size, as measured for example by light scattering. In embodiments, the average particle size is within one of the above ranges. In embodiments, 90% or more of the particles fall within one of the above ranges.

Other dyes that are anticipated to be useful, as can be confirmed as outlined herein, include without limitation:

TABLE

Dyes

Oil Red O (differing from Solvent Red 26 by an additional methyl in the right phenyl, para to the first methyl)
Sudan III (differing from Solvent Red 26 by lacking all three methyls)
Sudan Red 7B (differing from Sudan III by ethyl amino in place of hydroxy)
Sudan IV (differing from Solvent Red 26 by lacking the middle methyl in the structure as illustrated above)
Oil Yellow DE (N,N-diethyl-p-(phenylazo)aniline)
Solvent Blue 35 (1,4-bis(butylamino)anthraquinone)
Solvent Yellow 124 (N-Ethyl-N-[2-[1-(2-methylpropoxy)ethoxy]ethyl]-4-phenyldiazenylaniline)

Further dyes that are anticipated to be useful, as can be confirmed as outlined herein, include without limitation the solvent dyes in the following six tables, which dyes are available from Hangzhou Sunny Chemical Corp Ltd. (Hangzhou, China; sunnychemical.com):

TABLE

Blue Dyes

| | | |
|---|---|---|
| Solvent Blue B Base | Solvent Blue 4 | CAS#6786-83-0 |
| Solvent Blue BO Base | Solvent Blue 5 | CAS#1325-86-6 |
| Solvent Transparent Blue HB | Solvent Blue 11 | CAS#128-85-8 |
| Solvent Blue B | Solvent Blue 35 | CAS#17354-14-2 |
| Solvent Blue AP | Solvent Blue 36 | CAS#14233-37-5 |
| Solvent Fast Blue HBSN | Solvent Blue 38 | CAS#1328-51-4 |
| Solvent Transparent Blue S-RLS | Solvent Blue 45 | CAS#37299-23-5 |
| Solvent Oil Blue ZV | Solvent Blue 58 | CAS#61814-09-3 |
| Solvent Transparent Blue N | Solvent Blue 59 | CAS#6994-46-3 |
| Solvent Oil Blue GN | Solvent Blue 63 | CAS#6408-50-0 |
| Solvent Transparent Blue 2R | Solvent Blue 68 | CAS#4395-65-7 |
| Solvent Blue GL | Solvent Blue 70 | CAS#12237-24-0 |
| Solvent Blue GP | Solvent Blue 78 | CAS#2475-44-7 |
| Solvent Blue 2R | Solvent Blue 97 | CAS#61969-44-6 |
| Solvent Transparent Blue AG | Solvent Blue 101 | CAS#6737-68-4 |
| Solvent Blue 2B | Solvent Blue 104 | CAS#116-75-6 |
| Solvent Transparent Blue R | Solvent Blue 122 | CAS#67905-17-3 |
| Solvent Transparent Blue 3R | Solvent Blue 128 | |

TABLE

Yellow Dyes

| | | |
|---|---|---|
| Solvent Oil yellow G | Solvent Yellow 2 | CAS#60-11-7 |
| Solvent Fluorescent Yellow 8GF | Solvent Yellow 5 | CAS#85-84-7 |
| Solvent Oil Yellow R | Solvent Yellow 14 | CAS#842-07-9 |
| Solvent Oil Yellow 3G | Solvent Yellow 16 | CAS#4314-14-1 |
| Solvent Oil Yellow SG | Solvent Yellow 18 | CAS#6407-78-9 |
| Solvent Spirit Light Fast Yellow GR | Solvent Yellow 19 | CAS#10343-55-2 |
| Solvent Yellow BL | Solvent Yellow 21 | CAS#5601-29-6 |
| Solvent Oil Yellow GS | Solvent Yellow 28 | CAS#5844-01-9 |
| Solvent Yellow 4G | Solvent Yellow 33 | CAS#8003-22-3 |
| Solvent Auramine Base | Solvent Yellow 34 | CAS#492-80-8 |
| Solvent Fluorescent Yellow R | Solvent Yellow 43 | CAS#19125-99-6 |
| Solvent Oil Golden Yellow 2G | Solvent Yellow 56 | CAS#2481-94-9 |
| Solvent Transparent Yellow 2GH | Solvent Yellow 72 | CAS#61813-98-7 |
| Solvent Transparent Yellow G | Solvent Yellow 77 | CAS#2832-40-8 |
| Solvent Fast Yellow 2GL | Solvent Yellow 79 | CAS#12237-31-9 |
| Solvent Yellow KR | Solvent Yellow 82 | CAS#12227-67-7 |
| Solvent Transparent Yellow 3G | Solvent Yellow 93 | CAS#4702-90-3 |
| Solvent Fluorescent Yellow 3G | Solvent Yellow 98 | CAS#12671-74-8 |
| Solvent Yellow 3G | Solvent Yellow 114 | CAS#75216-45-4 |
| Solvent Fluorescent Yellow 9GF | Solvent Yellow 145 | CAS#27425-55-4 |
| Solvent Fluorescent Yellow 10GN | Solvent Yellow 160:1 | CAS#94945-27-4 |
| Solvent Transparent Yellow GS | Solvent Yellow 163 | CAS#13676-91-01 |
| Solvent Transparent Yellow 3GL | Solvent Yellow 176 | CAS#10319-14-9 |
| Solvent Transparent Yellow 6G | Solvent Yellow 179 | CAS#80748-21-6 |
| Solvent Fluorescent Yellow 10G | Solvent Yellow 185 | CAS#27245-55-4 |

TABLE

Orange Dyes

| | | |
|---|---|---|
| Solvent Oil Orange RC | Solvent Orange 2 | CAS#2646-17-5 |
| Solvent Chrysoidine Base | Solvent Orange 3 | CAS#495-45-5 |
| Solvent Oil Orange 45 | Solvent Orange 45 | CAS#13011-62-6 |
| Solvent Oil Orange KRV | Solvent Orange 54 | CAS#12237-30-8 |
| Solvent Oil Orange 3G | Solvent Orange 60 | CAS#61969-47-9 |
| Solvent Oil Orange R | Solvent Orange 62 | CAS#52256-37-8 |
| Solvent Transparent Orange 2G | Solvent Orange 63 | CAS#16294-75-0 |
| Solvent Oil Orange G | Solvent Orange 86 | CAS#81-64-1 |
| Solvent Oil Orange YR | Solvent Orange 99 | |
| Solvent Transparent Orange FR | Solvent Orange 105 | CAS#31482-56-1 |
| Solvent Transparent Orange R | Solvent Orange 107 | CAS#185766-20-5 |

TABLE

Red Dyes

| | | |
|---|---|---|
| Solvent Oil Red G | Solvent Red 1 | CAS#1229-55-6 |
| Solvent Fat Brown B | Solvent Red 3 | CAS#6535-42-8 |
| Solvent Oil Red GB | Solvent Red 8 | CAS#33270-70-1 |
| Solvent Transparent Scarlet H | Solvent Red 23 | CAS#85-86-9 |
| Solvent Oil Red B | Solvent Red 24 | CAS#85-83-6 |
| Solvent Transparent Red S | Solvent Red 25 | CAS#3176-79-2 |
| Solvent Oil Red TXN | Solvent Red 26 | CAS#4477-79-6 |
| Solvent Oil Red 5B | Solvent Red 27 | CAS#1320-06-5 |
| Solvent Rhodamine B Base | Solvent Red 49 | CAS#509-34-2 |
| Solvent Red 5B | Solvent Red 52 | CAS#81-39-0 |
| Solvent Transparent Red RL | Solvent Red 73 | |
| Solvent Spirit Fire Red B | Solvent Red 109 | CAS#53802-03-2 |
| Solvent Transparent Red GS | Solvent Red 111 | CAS#82-38-2 |
| Solvent Fast Fire Red G | Solvent Red 119 | CAS#12237-27-3 |
| Solvent Red 2BRN | Solvent Red 122 | CAS#12227-55-3 |
| Solvent Fast Red R | Solvent Red 124 | CAS#12239-74-6 |
| Solvent Red 2BL | Solvent Red 132 | CAS#61725-85-7 |
| Solvent Transparent Red EG | Solvent Red 135 | CAS#71902-17-5 |
| Solvent Transparent Red SB | Solvent Red 145 | CAS#66057-80-5 |
| Solvent Transparent Red FB | Solvent Red 146 | CAS#70956-30-8 |
| Solvent Transparent Red HFG | Solvent Red 149 | CAS#71902-18-6 |
| Solvent Red KLB | Solvent Red 168 | CAS#71832-19-4 |
| Solvent Transparent Red 2G | Solvent Red 169 | CAS#27354-18-3 |
| Solvent Transparent Red 3B | Solvent Red 172 | CAS#63512-13-0 |
| Solvent Transparent Red E-2G | Solvent Red 179 | CAS#89106-94-5 |
| Solvent Transparent Red 2B | Solvent Red 195 | CAS#164251-88-1 |
| Solvent Fluorescent Red BK | Solvent Red 196 | CAS#52372-36-8 |
| Solvent Fluorescent Red GK | Solvent Red 197 | CAS#52372-39-1 |
| Solvent Transparent Red CHA | Solvent Red 207 | CAS#15958-69-6 |
| Solvent Fast pink PR | Solvent Red 218 | CAS#82347-07-7 |
| Solvent Fluorescent Red 5B | Solvent Red 242 | CAS#22-75-8 |

TABLE

Violet Dyes

| | | |
|---|---|---|
| Solvent Oil Violet 5BN | Solvent Violet 8 | CAS#52080-58-7 |
| Solvent Methyl Violet 10B Base | Solvent Violet 9 | CAS#467-63-0 |
| Solvent Transparent Violet ER | Solvent Violet 11 | CAS#128-95-0 |
| Solvent Oil Violet B | Solvent Violet 13 | CAS#81-48-1 |
| Solvent Violet RS | Solvent Violet 14 | CAS#67577-84-8 |
| Solvent Transparent Violet 3B | Solvent Violet 26 | CAS#2872-48-2 |
| Solvent Violet RR | Solvent Violet 31 | CAS#70956-27-3 |
| Solvent Violet 3R | Solvent Violet 36 | CAS#61951-89-1 |
| Solvent Transparent Violet 2B | Solvent Violet 37 | CAS#61969-50-4 |
| Solvent Oil Violet 2R | Solvent Violet 56 | |
| Solvent Transparent Violet RL | Solvent Violet 59 | CAS#6408-72-6 |

TABLE

Green/Brown/Black Dyes

| | | |
|---|---|---|
| Solvent Green 5B | Solvent Green 3 | CAS#128-80-3 |
| Solvent Green S-G | Solvent Green 28 | CAS#71839-01-5 |
| Solvent Brown 2RL | Solvent Brown 43 | CAS#61116-28-7 |
| Solvent Transparent Black 4B | Solvent Black 3 | CAS#4197-25-5 |
| Solvent Oil Black BR | Solvent Black 5 | CAS#11099-03-9 |
| Solvent Oil Black NB | Solvent Black 7 | CAS#8005-02-5 |

TABLE-continued

| Green/Brown/Black Dyes | | |
|---|---|---|
| Solvent Black H | Solvent Black 27 | CAS#12237-22-8 |
| Solvent Black N | Solvent Black 29 | CAS#61901-87-9 |
| Solvent Black BC | Solvent Black 34 | CAS#32517-36-5 |

In embodiments of the invention, the dye of particles 182 is a dis azo disperse dye, such as red dye, and the liquid dye uniformly mixed in a first indicating layer 14 is an Anthraquinone based dye, such as green dye. In embodiments, these dyes are non-ionic and have low water solubility, such as being non-soluble.

In embodiments of the invention as illustrated in FIG. 1, exterior elastomeric layer is about 2 mil (51 mcm=micrometer) to about 40 mil (1016 mcm), such as about 7 mil (178 mcm). In embodiments, first indicating layer 14 is about 1 mil (25 mcm) to about 2 or about 4 mil (102 mcm) thick. Interior elastomeric layer 16 is, in embodiments, 2 mil (51 mcm=micrometer) to about 40 mil (1016 mcm), such as about 7 mil (178 mcm). In embodiments, the interior indicating layer is about 2 mile to about 4 mil thick, such as about 3 mil.

The first indicating layer can comprise polymer selected to have low chemical resistance to, or high swelling with, the chemical being detected. Such a polymer can be selected from a Chemical Resistance Guide, such as the one found at ansellpro.com/download/Ansell_8thEditionChemicalResistanceGuide.pdf, to identify polymers that have low chemical resistance to the chemical being detected. A terpolymer, which is non-cross linked, is a useful carrier polymer in the indicating layer. For example, a polyurethane terpolymer can be used. Data for polyurethane is available at k-mac-plastics.com/data%20sheets/polyurethane_chemical_resistance.htm. Low chemical resistance or high swelling can be achieved with reduced crosslinking.

Capillary action between glove layers can in embodiments assist in spreading the indicator spot beyond the site of the initial breach. This capillary effect can facilitate breach rapid breach detection, allowing the user to remove the damaged glove or other article and don a new glove or other article. Breach detection can be enhanced because of the greater area of dye spread can be more clearly visible.

Foam materials, such as open cell foam elastomers, can be used as polymer material in the first indicating layer 14.

The dye or pigment used in the first indicating layer can be any of the lysochrome dyes described above, but with the color selected to provide the contrast between the first indicating layer 14 and interior elastomeric layer 16 described above. In embodiments, the dye in layer 14 is an organic solvent soluble anthraquinone such as Solvent Green 33, Solvent Green 3, Solvent Green 28, and the like. In embodiments, the dye or pigment is green, and contrasts with a non-solvent soluble yellow mixture of organic and inorganic type pigment in the interior elastomeric layer 16. In embodiments, the indicator dye is blue or green, and the contrasting non-soluble pigment is red or yellow. Lack of solubility can be tested with for example MEK, acetone and THF. This contrasting can be added to the precursor of interior elastomeric layer 16 in paste form.

In embodiments, the first indicating layer 14 includes a significant polyurethane component (about 25% or more wt. of the polymer components of the layer), which can include a polyester polyurethane component. In embodiments, the polyurethane component comprises an aliphatic polyester polyurethane component, such as from an anionic aliphatic polyester polyurethane dispersion. In embodiments, a significant component is acrylic polymer and/or polychloroprene elastomer, which can be used in conjunction with another significant polymer having low chemical resistance, such as an appropriate polyurethane. Such an acrylic polymer can be a thermoplastic acrylic polymer, and can be from non-ionic thermoplastic acrylic polymer dispersion. In embodiments, the forming dispersion comprises anionic aliphatic polyester polyurethane dispersion (e.g., pH 6.5) and non-ionic thermoplastic acrylic polymer dispersion (e.g., pH 9.5). By "thermoplastic" in this context, it is meant a polymer with a glass transition temperature from about 4° C. to about 14° C.

The opacifying agent(s) in the first indicating layer 14 can include, for example, a hard wax (drop point ≥about 80, in embodiments to about 87° C.), white pigment (such as titanium dioxide, titanium calcium, calcium carbonate, zinc oxide, whiting, Lithopone or mixtures thereof). In embodiments, the opacifying agents comprise a mixture of hard wax and titanium dioxide. In embodiments, the hard wax is Montan wax (e.g., drop point 80-87° C., ISO 2176, s.g. 1.00-1.03 g/cm$^3$, Acid value of 135-160 mgKOH/g and Saponification value of 155-185 mgKOH/g). Montan wax is fossilized plant wax typically comprising non-glyceride long-chain (C4-C30) carboxylic esters (62-68%), free long-chain organic acids (22-26%), long-chain alcohols, ketones and hydrocarbons (7-15%) and resins. It typically has a melting point of approximately 82-95° C. In embodiments, the wax is has a high melting point in that the melting point is ≥about 75° C.

In embodiments, the first indicating layer 14 can be according to the following:

TABLE

| First Indicating Layer Formulation | | |
|---|---|---|
| Ingredient | Range (PHR) | Exemplary Amt. (PHR) |
| Elastomer(s) | 100 | 100 |
| Surfactant (e.g., SDS) | 2-5 | 3.85 |
| Opacifying Agent A | 6-8 | 7.5 |
| Opacifying Agent B (if present) | 6-8 | 7.5 |
| Dye or Pigment | 3-7 | 5.0 |
| Water | 80-92 | 92 |

In embodiments, the elastomers include acrylic polymer and/or chloroprene elastomer, for example in an amount from about 5 to about 10 PHR. There is no vulcanizing additives added to the acrylic or chloroprene in order to make the first layer easily decomposes or degrades upon solvent contact.

In embodiments, the interior elastomeric layer 16 includes less solvent soluble or non solvent soluble mixture of organic and/or inorganic colour pigments selected to help highlight the swelling or dissolution of the dye or pigment of the first indicating layer, or the swelling or dissolution of the first indicating layer 14. Examples of the non-solvent soluble color pigment include without limitation, CI Pigment Yellow 1, CI Pigment Yellow 3, CI Yellow 12, CI Yellow 14, CI Yellow 74, CI Yellow 83, CI Yellow 96 and the like. These International Color Index (CI) pigments are commonly available and used in the natural and synthetic latex products.

In embodiments, the interior elastomeric layer 16 is according to the following:

TABLE

Interior Elastomeric Layer Formulation

| Ingredient | Range (PHR) | Exemplary Amt. (PHR) |
|---|---|---|
| Elastomer(s) | 100 | 100 |
| Opacifying Agent (if present) | about 1.0-3.0 | about 2.0 |
| Dye or Pigment | about 0.2-2.0 | about 0.5 |
| Sulfur and vulcanizing agents | As appropriate | |
| Titrants | As appropriate | |
| Other Additives | As appropriate | |

The opacifying agent of the interior elastomeric layer 16 is titanium dioxide.

In embodiments, one or more of the layers (12, 14, 16, 18) have polymeric density consistent with aqueous latex dipping (as opposed for example to a density given polymer content consistent with injection molding). In certain embodiments, the barrier layers have other properties (such as elasticity) consistent, given polymer content, with aqueous latex dipping. These densities or other properties can vary with the polymer content of the elastomeric layers.

In embodiments, one or more of the elastomeric layers are made by aqueous dipping. In embodiments, one or more of the elastomeric layers has a property that distinguishes it from a layer formed by injection molding.

If the interior indicating layer 18 retains liner fibers, in embodiments it is made by dipping into a composite of latex dispersion and fibers. Methods for so forming from a composite dispersion are found in U.S. Pat. No. 7,037,579, and in U.S. App. No. 61/861,537, filed 2 Aug. 2013, the disclosures of which are incorporated herein as to their teachings on making such fibrous linings. In embodiments, a substantial part of the polymer of the composite is NBR. In embodiments, the NBR has a medium to high acrylonitrile content (about 33 to 42% wt.). In embodiments, the NBR is carboxylated. In embodiments, the flock is about 55-80% wt. hydrophobic flock, and about 20-45% hydrophilic flock, such as about 65% hydrophobic (e.g., cotton), 35% hydrophilic (e.g., modified rayon or cotton).

In embodiments, the interior indicating layer 18 is according to the following:

TABLE

Interior Elastomeric Layer Formulation

| Ingredient | Range (PHR) | Exemplary Amt. (PHR) |
|---|---|---|
| Elastomer(s) | 100 | 100 |
| Opacifying Agent (if present) | about 0.5-2.0 | about 1.0 |
| Acrylic thickener/binder | about 1-10 | about 1.5 |
| Pigment matching that of Layer 16 (if present) e.g. CI Y12 | about 0.15-0.25 | about 0.19 |
| Lysochrome dye particles | about 0.001-0.005 | about 0.003 |
| Flock | about 1.5-3.0 | about 2.0 |
| Polyolefin wax (e.g., 8-10 mcm) | 0.05-0.15 | 0.1 |
| Sulfur and vulcanizing agents | As appropriate | As appropriate |
| Dispersing agents | As appropriate | As appropriate |
| Other Additives, e.g., bactericides | As appropriate | As appropriate |

In embodiments, the article is a contamination indicating article (i.e., a splash protective article), whereby the exterior elastomeric layer is notably thinner, or made of a less chemically resistant polymer. For example, in embodiments there is no substantial resistant layer between the indicating layer and the outside of the article. By "no substantial resistant layer" it is meant that the permeation breakthrough time with respect to one of the selected chemicals is less than for interior elastomeric layer 16. Any embodiment that is described herein as having "no substantial resistant layer" can have this feature substituted with "no substantial resistant layer by thickness." By "no substantial resistant layer by thickness" it is meant that the thickness of any relevant non-substantial layers is about 1 mil or less, or about 0.5 mil or less. In embodiments, such a layer can be at least about 0.1 mil. Such non-substantial layers can have a polymer composition that is less resistant per mil thickness than the polymer composition of the interior elastomeric layer(s). In embodiments, a non-substantial layer can be of polyurethane or foamed polyurethane.

The interior of the glove can be treated to facilitate donning, manage moisture, or both. For example, the skin-contacting inner surface can be chlorinated, foamed, flocked, a combination thereof, or the like. A further interior layer 18 or 17 can comprise a silicone emulsion or a polymer coating. A further interior layer 18 or 17 can comprise a foamed or non-foamed adhesively-bonded cotton or rayon flock, or other fabric.

For use in the current invention, the first indicating 14 layer can be applied to an exterior elastomeric layer 12, for example of the type formed in dip coating methods. In the dip-coating process, the exterior elastomeric layer can be positioned on the former in an apparent interior orientation that will be inverted prior to use of the article. Or the interior elastomeric layer can be formed first, such that no net inversion is needed.

The first indicating layer can be uniformly applied to the elastomeric layer, or applied in discontinuous sections—so long as the density of segments located for breach or contamination indication is sufficient to provide the needed indicating color. For example, all or most of the palm-side surface of a glove, in the area of the palm and the fingers, can have indicating layer, while the dorsal side can have indicating layer in representative regions. Alternatively, for example, all of the area of the glove to the hand side of the wrist can have indicating layer.

A surface treatment, such as chlorination, siliconization, or a polymer coating can be applied to the article to reduce any inherent tackiness. A polymer coating process for example laminates the surface of the glove with a thin layer of synthetic polymer, normally up to several micrometers in thickness, having a low-friction coefficient value to provide anti-tack and good slip properties, as disclosed in Lai et al., U.S. Pat. No. 6,709,725, which discloses a natural or synthetic rubber elastomeric article having a coating layer containing a blend of a film-forming polymer and a wax. A further exterior layer (not shown) can serve to modify the surface tack that would apply with the polymer of exterior layer 12, and can provide a substrate for an anti-tack treatment.

In dip-coating methods it is anticipated that the solid particles of dye in the interior indicating layer 18 will be exposed to water, but shall resist solubilization. When contacted with latex that prior to dipping was alkali-stabilized, and when using alkali-sensitive dyes, it is anticipated that the use of latex coagulants or polymer binders with the dye will limit the exposure of the solid dye particles to alkali.

It has been found that diluted acid, wax and optionally anionic surfactant in the primer formulations minimizes dye or dye particle wet thermomigration effect in the removal of moisture during the curing process. Thus, the invention includes the method of dip-forming an elastomeric layer with a dye or dye particle wherein prior to dip-forming the layer onto another layer of elastomer, such a primer formulation is utilized. The acid can be, for example, acetic acid. The surfactant can be, for example, sodium lauryl sulfate. The wax can be, for example, Montan wax. The primer can be according to:

TABLE

| Wax Primer | |
| --- | --- |
| Ingredient | Wt. Range (wt. %) |
| Acid | about 3 to 8 |
| Calcium nitrate | about 1 to 6 |
| Surfactant | about 0.4 to 0.6 |
| Wax | about 0.1 to 0.3 |
| Bentonite clay | about 0.3 to 0.5 |
| Cellulose thickener | about 0.05 to 0.15 |
| Water | about 85 to 90 |

In embodiments, the surfactant of the primer can include an anionic surfactant such as sodium dodecyl sulfate (SDS), which does not promote dye wet thermomigration during article processing, and provides good surfactancy or effective wetting of primer on wet gelled elastomeric layers.

In embodiments, acid is included in the primer to provide strong immediate gelation on contact with the first indicator layer latex and also the interior indicator layer latex, and hence inhibits potential wet dye thermo migration.

In embodiments, the wax of the primer can be detected at a layer interface, even when the interface is with a first indicating layer 14 that contains wax, such as by concentration or by distribution into the adjoining layer.

The manufacturing process of an indicating article can have the following steps recited below (see FIG. 2). If needed, in step 202, a preliminary coagulant dip of a former can be conducted. In step 204, the exterior elastomeric layer 12 is formed. In step 206, an acid/primer dip can be conducted, e.g., utilizing a wax primer formulation as described above. In step 208, the former is dipped into a dispersion of low chemical resistance polymer, dye or pigment and opacifying agent for forming first indicating layer 14. Optionally there is another acid/primer dip between steps 208 and 210. In step 210, the former is dipped into the dispersion for forming interior elastomeric layer 16. The dispersion can include a dye or pigment for contrasting with the dye or pigment of first indicating layer 14. In step 212, an acid/primer dip can be conducted, e.g., utilizing a wax primer formulation as described above. In step 214, the former is dipped into a dispersion of polymer and lysochrome dye particles for forming interior indicating layer 18. The dispersion can include fibers for forming an interior lining for the article.

In certain embodiments, the invention comprises the exterior elastomeric layer 12, a first indicating layer 14 with a opacifying agent (as described above) and first dye or pigment, and an interior elastomeric layer 16 comprising a second dye or pigment selected to enhance the visual impact when color from the first dye or pigment is changed by interaction of the first indicating layer 14 with solvent. In embodiments, the article is effective to provide warning of ingress of the test chemicals. The method of making this embodiment can comprise steps 204, 208 and 210. In embodiments, the method further includes one or more of steps 202, 206 and 212.

In certain embodiments, the invention comprises the an elastomeric layer, such as layer 16, and a interior indicating layer 18 that includes liner fibers and lysochrome dye particles. The method of making this embodiment can include steps 210 and 214. In embodiments, the method further includes one or more of steps 202 (which can be used with a skip to step 210) and 212.

In embodiments, the invention relates to a method whereby a layer with a lysochrome dye, is formed onto another elastomeric layer, wherein after the dip forming the other elastomeric layer, the former is dipped into an acid/wax primer prior to the dip into the dispersion forming the layer with lysochrome dye. The lysochrome dye can be in a particle form that is optically of reduced visual impact because of its dispersion in appropriately sized particles, or in more dispersed and optically apparent form. The steps of the method can be steps 204, 206 and 208*. Step 208* uses a polymer dispersion that includes the lysochrome dye, and may or may not include an opacifying agent. In embodiments, an opacifying agent is included.

The thickness of a given layer of the glove can be built up by several dips with or without additional use of coagulant such as calcium nitrate (typically applied to the former prior to dipping).

Alternatively, a dip process can begin with an interior layer, and build the layers outwards.

In embodiments, the breach or contamination indicating glove is used in conjunction with a laminated LCP (liquid crystal polymer) multilayer film, such as the film of the Barrier 2-100 (5 layers) sold by Ansell Ltd. (Richmond, AU). An above-described article of the invention is worn on the interior of an article of laminated LCP multilayer film. In embodiments, the above-described article of the invention is bonded to the laminated LCP multilayer film, such as by adhesive layer or by thermal bonding. Thermal bonding can be conducted through the above-described article to minimize any compromise to the laminated LCP multilayer film. A process utilizing a non-tacky, thermoplastic adhesive layer between the laminated LCP multilayer film and the above-described article, whereby infrared light is used to fuse the adhesive after inflating the elastomeric above-described article, can be used. Such a process is as described in U.S. Pat. No. 7,803,438, which description is incorporated herein in its entirety. Inflating the interior article assures good contact between the two articles when adhered.

In this fashion, the contamination indicating function can be used with the broad chemical resistance of laminated LCP multilayer film.

The articles that can incorporate the indicating feature of the invention include gloves, other protective wear such as aprons, chemical hazard suits (or parts thereof such as pants, jackets, sleeve guards, head coverings, or the like), non-clothing flexible shields or dams, and the like. All such articles can have breach indicating or contamination/splash indicating.

In embodiments, the article is a pursuant to any embodiment described herein and is a patch with an adhesive interior coating so that the patch can be applied to another piece of protective clothing. For example, the patch can be applied to chemical hazard suit, such as at a splash prone area, such as on the wrist, upper arm, leg or the like. The adhesive layer can be a pressure-sensitive adhesive, which prior to use can be covered with a release liner. The adhesive layer can for example be applied to the article by one side of a thin two sided adhesive tape (e.g., from 3M). Or, for example, the adhesive layer can be a structural adhesive requiring activation, such as by infrared radiation (for a thermoplastic adhesive). In the pressure-sensitive case, the bond can be strong, such that it cannot readily be removed, or can be such that the article can be peeled off the underlying clothing. For structural adhesives, in some cases the activator can be reapplied to facilitate removal (such as infrared radiation).

A number of thermoplastic adhesive systems are available that stretch from about 10-100%, which stretching can be useful in the current invention. These include low molecular weight polyethylene (mp=110° C.), polyester (mp=120° C.), ethylene vinyl acetate (mp=121° C.), ethylene 2-ethyl hexyl acrylate polymer, EEHA (mp=125° C.), and thermoplastic polyurethane, such as RTP-2300 A (mp=111° C.) from RTP Co., Winona, Minn. These polymers can be sprayed as a molten liquid and solidify as a non-tacky layer suitable for use in the context of the present invention.

In embodiments, the article is a pursuant to any embodiment described herein and is band that is configured to snuggly fit around an arm, finger, leg, or the like.

One useful embodiment for a patch or band has first indicating layer 14 and an interior elastomeric layer 16, and at most a thin exterior elastomeric layer 12. This is because in many uses a rapid indication of chemical splash is desired. If a patch, it will generally have an adhesive layer 22 (FIG. 4).

In use, when the patch or band indicates contamination, a user of a chemical protective outfit can wind down his or her activity in a hazardous area. The patch or band can be removed, and the chemical protective outfit sent for washing to remove chemical contaminants.

All ranges recited herein include ranges therebetween, and can be inclusive or exclusive of the endpoints. Optional included ranges are from integer values therebetween (or inclusive of one original endpoint), at the order of magnitude recited or the next smaller order of magnitude. For example, if the lower range value is 0.2, optional included endpoints can be 0.3, 0.4, . . . 1.1, 1.2, and the like, as well as 1, 2, 3 and the like; if the higher range is 8, optional included endpoints can be 7, 6, and the like, as well as 7.9, 7.8, and the like. One-sided boundaries, such as 3 or more, similarly include consistent boundaries (or ranges) starting at integer values at the recited order of magnitude or one lower. For example, 3 or more includes 4 or more, or 3.1 or more.

The invention further includes the following embodiments:

Embodiment 1

A breach or contamination indicating elastomeric article for indicating a breach or contamination by a selected chemical or group of chemicals, the article having an exterior and interior and comprising: an interior elastomeric layer selected to resist permeation by the selected chemical(s); and exterior thereto, a contiguous or dis-contiguous first indicating layer comprising a first dye or pigment and an opacifying agent, the dye or pigment providing the layer with color, the first indicating layer changing color and/or opacity when contacted with a selected chemical such regions of the article where the layer is so contacted contrast with non-contacted regions.

Embodiment 2

The breach or contamination indicating elastomeric article of Embodiment 1, further comprising an contiguous or dis-contiguous interior indicating layer, situated interior to the interior elastomeric layer, which interior indicating layer comprises particles of a lysochrome dye, the particles selected to become more visually impactful as a selected chemical penetrates to contact lysochrome dye particles.

Embodiment 3

The breach or contamination indicating elastomeric article of Embodiment 2, wherein the interior indicating layer anchors fibers for an interior liner, the fibers configured to improve comfort for a user and/or moisture dispersion from a user.

Embodiment 4

The breach or contamination indicating elastomeric article of Embodiment 3, wherein the fibers comprise about 55-80% wt. hydrophobic flock, and about 20-45% hydrophilic flock.

Embodiment 5

The breach or contamination indicating elastomeric article of one of Embodiments 1 to 4, wherein the first indicating layer is formed of polymer(s) with a net low chemical resistance.

Embodiment 6

The breach or contamination indicating elastomeric article of one of Embodiments 1 to 5, wherein first indicator layer polymers include a substantial amount of thermoplastic acrylic polymer.

Embodiment 7

The breach or contamination indicating elastomeric article of one of Embodiments 1 to 6, wherein the opacifying agent comprises a hard wax.

Embodiment 8

The breach or contamination indicating elastomeric article of one of Embodiments 1 to 7, wherein the opacifying agent comprises or further comprises a white pigment.

Embodiment 9

The breach or contamination indicating elastomeric article of one of Embodiments 2 to 8, wherein an interface between the interior indicating layer and an adjacent elastomeric layer comprises wax.

Embodiment 10

The breach or contamination indicating elastomeric article of one of Embodiments 1 to 9, wherein the interior elastomeric layer comprising a second dye or pigment selected to enhance visual impact when color from the first dye or pigment is changed by interaction of the first indicating layer with solvent.

Embodiment 11

The breach or contamination indicating elastomeric article of one of Embodiments 1 to 10, further comprising an exterior elastomeric layer, situated exterior to the first indicating layer, the layer configured to resist penetration by the selected chemical(s).

Embodiment 12

The contamination indicating elastomeric article of Embodiment 1 that is a patch or band, optionally further according to one or more of Embodiments 5 to 10.

Embodiment 13

A breach or contamination indicating elastomeric article for indicating a breach or contamination by a selected chemical or group of chemicals, the article having an exterior and interior and comprising: an elastomeric layer selected to resist permeation by the selected chemical(s); interior thereto, a contiguous or dis-contiguous interior indicating layer, which interior indicating layer comprises particles of a lysochrome dye, the particles selected to become more visually impactful as a said selected chemical penetrates to contact lysochrome dye particles; and one or more of:
  (a) between the elastomeric layer and the interior indicating layer, a wax residue of a wax primer; and
  (b) wherein the interior indicating layer anchors fibers for an interior liner, the fibers configured to improve comfort for a user and/or moisture dispersion from a user.

Embodiment 14

The breach or contamination indicating elastomeric article of Embodiment 13, wherein an interface between the interior indicating layer and an adjacent elastomeric layer comprises wax.

Embodiment 15

The breach or contamination indicating elastomeric article of Embodiment 13, wherein the interior indicating layer anchors fibers for an interior liner, the fibers configured to provide comfort for a user and/or moisture dispersion from a user.

Embodiment 16

A method of making an article of one of Embodiments 1 to 12, comprising: dipping a former (which may have previously been dipped to form coagulated latex layers) into a polymer dispersion for forming an elastomeric layer, which may be the interior elastomeric layer; and further dipping the former into a polymer dispersion comprising the dye and opacifying agent for forming the first indicating layer.

Embodiment 17

The method of Embodiment 16, further comprising, between the elastomeric layer dip and the first indicating layer dip, dipping into a wax and diluted acid primer.

Embodiment 18

A method of making an article of one of Embodiments 13 to 15, comprising: dipping a former (which may have previously been dipped to form coagulated latex layers) into a polymer dispersion for forming the elastomeric layer; and further dipping the former into a polymer dispersion comprising the lysochrome dye particles, wherein if the interior indicating layer anchors fibers, the fibers are applied as part of a composite dispersion with the lysochrome dye particles.

Embodiment 19

The method of Embodiment 18, further comprising, between the elastomeric layer dip and the interior indicating layer dip, dipping into a wax and diluted acid primer.

Embodiment 20

A method of forming an indicating layer for a breach or contamination indicating elastomeric article comprising: dipping a former (which may have previously been dipped to form coagulated latex layers) into a polymer dispersion for forming an elastomeric layer; further dipping the former into a wax and diluted acid primer; and further dipping the former into a polymer dispersion comprising the lysochrome dye.

Publications and references, including but not limited to patents and patent applications, cited in this specification are herein incorporated by reference in their entirety in the entire portion cited as if each individual publication or reference were specifically and individually indicated to be incorporated by reference herein as being fully set forth. Any patent application to which this application claims priority is also incorporated by reference herein in the manner described above for publications and references.

What is claimed is:

1. A breach or contamination indicating elastomeric article for indicating a breach or contamination by one or more organic solvents, the article having an exterior and interior and comprising:
    an interior elastomeric layer configured to resist permeation by the one or more organic solvents; and
    exterior thereto, a contiguous or dis-contiguous polymeric first indicating layer comprising layer-forming polymer(s), a first dye or pigment and one or more opacifying agents, the dye or pigment and opacifying agents dispersed in the first indicating layer, the dye or pigment providing the first indicating layer with color, the first indicating layer changing color tone when contacted with the one or more organic solvents such that regions of the article where the first indicating layer is so contacted contrast with non-contacted regions, wherein the first indicating layer is formed of the layer-forming polymer(s), which polymers are configured to be swellable when contacted with xylene, butyl acetate, Methyl Isobutyl Ketone (MIBK), acetone and toluene, wherein the one or more opacifying agents comprise a wax with a melting point of about 75° C. or higher and an opacifying pigment.

2. The breach or contamination indicating elastomeric article of claim 1, further comprising a contiguous or dis-contiguous interior polymeric indicating layer, situated interior to the interior elastomeric layer, which interior indicating layer comprises particles of a lysochrome dye directly embedded in the polymer of the interior indicating layer, the particles configured to provide separate points of coloration to provide a visual warning to a user as the one or more organic solvents penetrates to contact lysochrome dye particles.

3. The breach or contamination indicating elastomeric article of claim 2, wherein the interior indicating layer anchors fibers for an interior liner, the fibers configured to improve comfort for a user and/or moisture dispersion from a user.

4. The breach or contamination indicating elastomeric article of claim 3, wherein the fibers comprise about 55-80% wt. hydrophobic flock, and about 20-45% hydrophilic flock.

5. The breach or contamination indicating elastomeric article of claim 3, further comprising an exterior elastomeric layer, situated exterior to the polymeric first indicating layer, the exterior elastomeric layer configured to resist penetration by the one or more organic solvent(s).

6. The breach or contamination indicating elastomeric article of claim 5, wherein the one or more opacifying agents comprise a wax with a melting point of about 75° C. or higher and an opacifying pigment.

7. The breach or contamination indicating elastomeric article of claim 2, further comprising an exterior elastomeric layer, situated exterior to the polymeric first indicating layer, the exterior elastomeric layer configured to resist penetration by the one or more organic solvents.

8. The breach or contamination indicating elastomeric article of claim 7, wherein the one or more opacifying agents comprise a wax with a melting point of about 75° C. or higher and an opacifying pigment.

9. The breach or contamination indicating elastomeric article of claim 1, wherein polymeric first indicator layer polymers include 25% or more by weight of thermoplastic acrylic polymer.

10. The breach or contamination indicating elastomeric article of claim 1, wherein the opacifying pigment comprises a white inorganic pigment.

11. The breach or contamination indicating elastomeric article of claim 1, wherein the interior elastomeric layer comprises a second dye or pigment that enhances visual impact when color tone from the polymeric first indicating layer is changed by interaction of the first indicating layer with solvent.

12. The breach or contamination indicating elastomeric article of claim 1, further comprising an exterior elastomeric layer, situated exterior to the first indicating layer, the exterior elastomeric layer configured to resist penetration by the one or more organic solvent(s).

13. The breach or contamination indicating elastomeric article of claim 1, which article is a contamination indicating article and is a patch or band.

14. A method of making an article of claim 1, comprising:
dipping a former into a polymer dispersion for forming an elastomeric layer;
thereafter dipping the former into a polymer dispersion comprising the dye and the one or more opacifying agents for forming the first indicating layer;
between the elastomeric layer dip and the first indicating layer dip, dipping the former into primer comprising wax and diluted acid; and
vulcanizing the formed indicating layer and elastomeric layer to form the breach or contamination indicating elastomeric article.

15. A breach or contamination indicating elastomeric article for indicating a breach or contamination by one or more organic solvents, the article having an exterior and interior and comprising:
a first elastomeric layer configured to resist permeation by the one or more organic solvents;
interior thereto, a contiguous or dis-contiguous interior polymeric indicating layer, which interior indicating layer comprises particles of a lysochrome dye directly embedded in the polymer of the interior indicating layer, the particles configured to provide separate points of coloration to provide a visual warning to a user as the one or more organic solvents penetrate to contact lysochrome dye particles;
wherein the interior indicating layer anchors fibers for an interior liner, the fibers configured to improve comfort for a user and/or moisture dispersion from a user; and
wherein the interior polymeric indicating layer is the most interior polymeric layer.

16. A method of making an article of claim 15, comprising:
dipping a former into a polymer dispersion for forming the elastomeric layer;
thereafter dipping the former into a polymer dispersion comprising the lysochrome dye particles to form the interior polymeric indicating layer, wherein, the fibers are applied as part of a composite dispersion of fibers and polymers along with the lysochrome dye particles; and
vulcanizing the formed indicating layer and elastomeric layer to form the breach or contamination indicating elastomeric article.

17. The method of claim 16, further comprising, between forming the elastomeric layer by dipping and forming the interior polymeric indicating layer by dipping, dipping the former into primer comprising wax and diluted acid.

18. A method of forming an indicating layer for a breach or contamination indicating elastomeric article comprising:
dipping a former into a polymer dispersion for forming an elastomeric layer;
thereafter dipping the former into a primer comprising wax and diluted acid;
thereafter dipping the former into a polymer dispersion comprising lysochrome dye for forming the indicating layer; and
vulcanizing the formed indicating layer and elastomeric layer to form the breach or contamination indicating elastomeric article.

* * * * *